United States Patent [19]

Song et al.

[11] Patent Number: 4,789,547

[45] Date of Patent: Dec. 6, 1988

[54] TRANSDERMAL MATRIX SYSTEM

[75] Inventors: Suk-Zu Song, Flanders; Surendra C. Mehta, Randolph; Zahra A. Rashidbaigi, Nutley; Russell U. Nesbitt, Somerville; Mahdi B. Fawzi, Flanders, all of N.J.

[73] Assignee: Warner-Lambert Company, Morris Plains, N.J.

[21] Appl. No.: 63,204

[22] Filed: Jun. 17, 1987

[51] Int. Cl.$^4$ .............................................. A61F 13/00
[52] U.S. Cl. .................................... 424/449; 424/448
[58] Field of Search ........................... 424/81, 448, 449

[56] References Cited

U.S. PATENT DOCUMENTS

| | | | |
|---|---|---|---|
| 3,567,118 | 3/1971 | Shepherd et al. | 424/81 |
| 4,056,496 | 11/1977 | Mancini et al. | 424/81 |
| 4,226,848 | 10/1986 | Yoshida | 424/434 |
| 4,250,163 | 2/1981 | Nagai | 424/434 |
| 4,359,483 | 11/1982 | Katesu | 427/2 |
| 4,423,099 | 12/1983 | Mueller | 428/85 |
| 4,435,412 | 3/1984 | Girijavallabhan | 514/192 |
| 4,435,413 | 3/1984 | McCombie | 514/192 |
| 4,452,892 | 6/1984 | Rosevear | 435/176 |
| 4,563,182 | 1/1986 | Stoy | 604/285 |
| 4,575,539 | 3/1986 | DeCosta et al. | 424/81 |
| 4,666,703 | 5/1987 | Kopf | 424/81 |
| 4,668,506 | 5/1987 | Bawa | 424/429 |

OTHER PUBLICATIONS

U.S. patent application Ser. No. 900,865, filed Aug. 27, 1986, (PD-3371), M. Mahjour, et al.

*Primary Examiner*—Thurman K. Page
*Assistant Examiner*—L. R. Horne
*Attorney, Agent, or Firm*—Ronald A. Daignault

[57] ABSTRACT

A composition for the transmembranal, including transdermal, administration of a pharmaceutical preparation comprising cross-linked carboxymethylcellulose, an alcohol soluble poly (2-hydroxyethyl) methacrylate), a permeation enhancer, such as a mixture of linoleic acid and propylene glycol, and a biologically active material, as well as a device for administering the aforementioned composition to mammals, and also a method for administering transdermally to a mammal an effective amount of the aforementioned composition.

23 Claims, No Drawings

TRANSDERMAL MATRIX SYSTEM

BACKGROUND OF THE INVENTION

Cross-linked carboxymethylcellulose in combination with an alcohol soluble poly (2-hydroxyethyl methacrylate) (p-HEMA) and a permeation enhancer, such as a mixture of linoleic acid and propylene glycol, forms a hydrogel capable of delivering therapeutic levels of biologically active materials through mammalian membranes.

Transdermal drug delivery is the diffusion of a therapeutic agent into and through the skin of a mammal. It is an alternative route of administration to oral delivery of various drugs. Advantages of this type of delivery system over oral administration include lack of gastrointestinal problems, reduction of drug metabolism due to initial bypass of the liver, and the ability to continually deliver a systemic amount of a drug over a controlled period of time.

U.S. Pat. No. 4,563,182 to Stoy, V. A. and Stoy, G. B., issued Jan. 7, 1986 discloses a method of treating hemorrhoids using a rectal insert which contains a frozen hydrogel; U.S. Pat. No. 4,452,892 to Rosevear, A., issued June 5, 1984 discloses the use of a hydrogel system containing various immobilized biologically active species; U.S. Pat. No. 4,423,099 to Mueller, K. F. and Heiber, S. J., issued Dec. 27, 1983 discloses a nonuniform water insoluble interpenetrating polymer blend composition useful for the controlled delivery of active ingredients such as fragrances and bio-affecting agents; U.S. Pat. No. 4,359,483 to Kaetsu, I. and Yoshida, M., issued Nov. 16, 1982 discloses a multi-layered slow release composite; U.S. Pat. No. 4,226,848 issued Oct. 7, 1986 and its divisional U.S. Pat. No. 4,250,163 issued Feb. 10, 1981, to Nagai, T., et al disclose a pharmaceutical preparation which adheres to the mucosa of the oral or nasal cavity. The aforementioned disclosures describe various polymeric materials used as inert carriers for active substances and which in some cases are controllably released from these carriers. However, they differ from the present invention in that they do not describe the combination of cross-linked carboxymethylcellulose with an alcohol soluble poly (2-hydroxyethyl methacrylate) (p-HEMA) and a permeation enhancer, such as a mixture of linoleic acid and propylene glycol to form a hydrogel capable of delivering therapeutic levels of biologically active materials through mammalian membranes.

SUMMARY OF THE INVENTION

The present invention relates to a novel composition for the transmembranal, including transdermal, administration of a pharmaceutical preparation comprising cross-linked carboxymethylcellulose, an alcohol soluble poly (2-hydroxyethyl methacrylate) (p-HEMA), a permeation enhancer, and a biologically active material.

A more preferred composition relates to a novel transdermal matrix preparation comprising cross-linked carboxymethylcellulose, a one to four carbon alcohol soluble poly (2-hydroxyethyl methacrylate) (p-HEMA), a permeation enhancer comprising a saturated or unsaturated fatty acid containing from eight to twenty-four carbon atoms and a solvent selected from the group consisting of propylene glycol, glycerol, ethanol, triacetin, triethyl citrate, dimethylisosorbide, ethylene glycol and propoxylated cetyl alcohol, and a biologically active material.

A most preferred composition relates to a novel transdermal matrix preparation comprising cross-linked carboxymethyl cellulose, isopropyl alcohol soluble poly (2-hydroxyethyl methacrylate), a permeation enhancer, such as a mixture of linoleic acid and propylene glycol and a biologically active material, such as, for example, 8-hydroxy-5-[1-hydroxy-2-[(1-methylethyl)amino]-butyl]-2(1$\underline{H}$)-quinolinone monohydrochloride or 4,5-dihydro-6-[4-(1$\underline{H}$-imidazol-1-yl)phenyl]-5-methyl-3(2$\underline{H}$)-pyridazinone monohydrochloride.

8-hydroxy-5-[1-hydroxy-2-[(1-methylethyl)amino]-butyl]-2(1$\underline{H}$)-quinolinone monohydrochloride, also known as procaterol, is a known bronchodilator and selective beta-adrenergic agonist. The compound and its preparation are described in U.S. Pat. No. 4,026,897, which is hereby incorporated by reference.

4,5-Dihydro-6-[4-(1$\underline{H}$-imidazol-1-yl)phenyl]-5-methyl-3(2$\underline{H}$)-pyridazinone monohydrochloride is a known cardiotonic agent. The compound and its preparation are described in U.S. Pat. No. 4,353,905, which is hereby incorporated by reference.

The present invention is also directed to a device for administering the aforementioned compositions transdermally to a mammal.

The present invention is further directed to a method for administering transdermally to a mammal an effective amount of the aforementioned compositions.

DETAILED DESCRIPTION OF THE INVENTION

Typically a transdermal drug delivery system consists of a multilayer laminate device. The device consists of an impermeable backing, whose perimeter contains an adhesive, and a matrix system comprising a composition of a drug component admixed in a polymeric hydrogel layered on the inside of the backing. The matrix system swells in water, and is capable of delivering the drug through mammalian skin, including human skin, over a controlled period of time.

The impermeable backing to be used to support the matrix system should be a strong flexible material so that a bandage, foil or other suitable supportive structure could be fashioned using it. Suitable materials include aluminum, metallized polyester, polyurethane, polyethylene, and the like.

The perimeter of the impermeable backing contains a silicone or acrylic medicinal grade adhesive laminate on the backing for sticking to cutaneous tissue.

The novel matrix system of the present invention contains three components: (1) a carrier component, (2) a permeation enhancement component, and (3) a drug component.

The carrier component contains one or more substantially inert ingredients which function to give the composition physical properties such that it can be effectively administered transmembranally. The carrier component of the present invention comprises about one to about fifteen percent by weight of cross-linked carboxymethylcellulose (CLD2 (x-linked carboxymethylcellulose) (Buckeye Cellulose Corporation)) and about fifteen to about forty percent by weight of an alcohol soluble poly (2-hydroxyethyl methacrylate) and most preferably about seven percent by weight of cross-linked carboxymethylcellulose and about twenty-seven percent by weight of an alcohol soluble poly (2-hydroxyethyl methacrylate).

The alcohol soluble poly (2-hydroxyethyl methacrylate) is prepared by mixing one part of high purity 2-hydroxyethyl methacrylate (Optical Monomer Corporation) with four parts by volume of an alcohol containing from one to four carbon atoms, such as, for example, isopropyl alcohol. Azobisisobutyronitrile, 0.06 percent weight/volume, is dissolved in the aforementioned mixture. The mixture is heated at 60° C. for twenty-four hours and the alcohol soluble poly (2-hydroxyethyl methacrylate) is obtained either by removing the alcohol by evaporation or by precipitation from the alcohol solution by the addition of diethylether.

The permeation enhancement component is a substance or a combination of substances which increases the amount of the drug component or components that are transported across biological membranes and into the bloodstream. The permeation enhancement component comprises at least one essential saturated or unsaturated fatty acid, containing from eight to twenty-four carbon atoms, such as, linoleic, or oleic acid comprising about one to about fifteen percent by weight and most preferably about seven percent by weight of linoleic acid. Further the permeation enhancement component contains at least one solvent for the drug component, such as, propylene glycol, glycerol, ethanol, triacetin, triethyl citrate, dimethylisosorbide, ethylene glycol, propoxylated cetyl alcohol, and the like comprising about twenty to about eighty percent by weight and most preferably about sixty percent by weight of propylene glycol.

While the above permeation enhancement components are preferred, certain drugs may be transported across biological membranes using only the aforementioned solvents without a saturated or unsaturated fatty acid.

The drug component, such as, for example, procaterol or a pharmaceutically acceptable salt thereof or 4,5-dihydro-6-[4-(1H-imidazol-1-yl) phenyl]-5-methyl-3(2H)-pyridazinone or a pharmaceutically acceptable salt thereof, comprises about one-half to about five percent by weight and most preferably about two percent by weight of procaterol or 4,5-dihydro-6-[4-(1H-imidazol-1-yl) phenyl]-5-methyl-3(2H)-pyridazinone or a pharmaceutically acceptable salt thereof.

The dosage levels to be used in administering the instant compositions containing procaterol or 4,5-dihydro-6-[4-(1H-imidazol-1-yl)phenyl]-5-methyl-3(2H)-pyridazinone are generally consistent with those disclosed in U.S. Pat. Nos. 4,026,897 and 4,353,905.

While procaterol or a pharmaceutically acceptable salt thereof or 4,5-dihydro-6-[4-(1H-imidazol-1-yl)phenyl]-5-methyl-3(2H)-pyridazinone or a pharmaceutically acceptable salt thereof is used as an example of a bronchodilator and a cardiotonic agent the present invention also includes other bronchodilators and cardiotonic agents as well as drugs that need to be delivered systemically. Thus, sedatives, tranquilizers, antihistamines, cognition activators, antihypertensives, analgesics, antiarrhythmics, peptides, and the like may be included in the compositions of the present invention.

Other conventional adjuncts, such as, colorants, perfumes, stabilizers, and the like can be employed in suitable quantities in the compositions of the present invention.

The novel matrix system of the present invention is useful in the preparation of various devices by which therapeutic agents can be administered transmembranally to mammals. Useful delivery devices include patches, films, sprays, swabs, suppositories, creams, gels and the like with or without supportive backing materials.

The invention is further illustrated but not limited by the following examples.

EXAMPLE 1

Transdermal Patch Containing Procaterol Monohydrochloride

Component
Drug: 2 percent by weight concentration of procaterol monohydrochloride in solution
Polymer:
  1 part by weight cross-linked carboxymethylcellulose
  4 parts by weight alcohol soluble poly (2-hydroxyethyl methacrylate)
Liquid Formulation:
  10 parts by weight linoleic acid
  90 parts by weight propylene glycol
Ratio of Liquid to Polymers: 2

Procaterol monohydrochloride is dissolved in a mixture of linoleic acid and propylene glycol. To this mixture is added pulverized alcohol soluble poly (2-hydroxyethyl methacrylate) and cross-linked carboxymethylcellulose. The mixture is stirred well with a mechanical stirrer and the viscous material is applied as a film on adhesive tape.

EXAMPLE 2

Transdermal Patch Containing 4,5-Dihydro-6-[4-(1H-imidazol-1-yl)phenyl]-5-methyl-3(2H)-pyridazinone Monohydrochloride Component
Drug: 3 percent by weight concentration of 4,5-dihydro-6-[4-(1H-imidazol-1-yl)phenyl]-5-methyl-3(2H)-pyridazinone monohydrochloride in solution
Polymer:
  1 part by weight cross-linked carboxymethylcellulose
  4 parts by weight alcohol soluble poly (2-hydroxyethyl methacrylate)
Liquid Formulation:
  10 parts by weight linoleic acid
  90 parts by weight propylene glycol
Ratio of Liquid to Polymers: 2

The afoementioned components are combined in a process analogous to Example 1 to form a transdermal patch.

Diffusion Experiment:

In vitro diffusion experiments were carried out utilizing the matrix compositions of Example 1 and Example 2.

Abdominal or back sections from hairless mouse (seven to eight weeks old) skin are mounted on standard Franz ® diffusion cells with the stratum corneum facing the donor compartment. The receiver compartment is filled with warm saline solution (37° C.).

The solution is stirred continuously by a magnetic stirrer at constant speed using a magnetic stirring bar. The transdermal patch containing the matrix composition is applied on the skin. The transport of the drug cross the membrane to the receiver solution is monitored by withdrawing the entire volume of the receiver compartment at timed intervals and analyzing for drug by high performance liquid chromatography (HPLC).

After each sampling interval the receiver compartment is filled with fresh solvent.

In the experiment, the amount of drug passing through the membrane into the receiver compartment is plotted as a function of time. This transport profile, after initial delay, becomes linear when steady state flux is reached. Extrapolation of this line to zero amount of drug transport, intersects the time axis. This intersect is defined as the lag time.

The results are shown in the following table.

TABLE

Diffusion of Drugs Through Hairless Mouse Skin

| Example | Flux* (mg/10 cm$^2$/day) | Lag Time (hours) |
|---------|--------------------------|------------------|
| 1       | 17.3                     | 1.3              |
| 2       | 2.39                     | 1.5              |

*Flux is the amount of drug passing from a unit area through the barrier over a period of time.

We claim:

1. A composition for the transdermal administration of a pharmaceutical preparation comprising cross-linked carboxymethylcellulose, an alcohol soluble poly (2-hydroxyethyl methacrylate), at least one permeation enhancer, and a biologically active material.

2. A composition of claim 1 where the alcohol soluble poly (2-hydroxyethyl methacrylate) is a one to four carbon alcohol soluble poly (2-hydroxyethyl methacrylate).

3. A composition of claim 1 where the alcohol soluble poly (2-hydroxyethyl methacrylate) is isopropyl alcohol soluble poly (2-hydroxyethyl methacrylate).

4. A composition of claim 1 where the permeation enhancer consists of a saturated or unsaturated fatty acid containing from eight to twenty-four carbon atoms and a solvent selected from the group consisting of propylene glycol, glycerol, ethanol, triacetin, triethyl citrate, dimethylisosorbide, ethylene glycol and propoxylated cetyl alcohol.

5. A composition of claim 1 where the permeation enhancer is lirnoleic acid and propylene glycol.

6. A composition of claim 1 where the biologically active material is a sedative.

7. A composition of claim 1 where the biologically active material is a tranquilizer.

8. A composition of claim 1 where the biologically active material is an antihistamine.

9. A composition of claim 1 where the biologically active material is a cognition activator.

10. A composition of claim 1 where the biologically active material is an antihypertensive.

11. A composition of claim 1 where the biologically active material is an analgesic.

12. A composition of claim 1 where the biologically active material is an antiarrhythmic.

13. A composition of claim 1 where the biologically active material is a cardiotonic.

14. A composition of claim 1 where the biologically active material is a bronchodilator.

15. A composition of claim 1 where the biologically active material is a peptide.

16. A composition of claim 1 where the biologically active material is 8-hydroxy-5-[1-hydroxy-2-[(1-methylethyl)amino]butyl]-2(1H)-quinolinone or a pharmaceutically acceptable salt thereof.

17. A composition of claim 1 where the biologically active material is 4,5-dihydro-6-[4-(1H-imidazol-1-yl)phenyl]-5-methyl-3(2H)pyridazinone or a pharmaceutically acceptable salt thereof.

18. A device for administering the composition of claim 1 transdermally to a mammal.

19. A device for administering the composition of claim 16 transdermally to a mammal.

20. A device for administering the composition of claim 17 transdermally to a mammal.

21. A method for administering transdermally to a mammal an effective amount of the composition of claim 1.

22. A method for administering transdermally to a mammal an effective amount of the composition of claim 16.

23. A method for administering transdermally to a mammal an effective amount of the composition of claim 17.

* * * * *

UNITED STATES PATENT AND TRADEMARK OFFICE
CERTIFICATE OF CORRECTION

PATENT NO. : 4,789,547
DATED : December 6, 1988
INVENTOR(S) : Suk-Zu Song et al

It is certified that error appears in the above—identified patent and that said Letters Patent is hereby corrected as shown below:

In column 5, line 44,
  delete "lirnoleic" and
  insert -- linoleic --.

Signed and Sealed this

Nineteenth Day of December, 1989

*Attest:*

JEFFREY M. SAMUELS

*Attesting Officer*     *Acting Commissioner of Patents and Trademarks*